(12) United States Patent
Zawierucha et al.

(10) Patent No.: US 8,536,096 B2
(45) Date of Patent: Sep. 17, 2013

(54) METHOD FOR CONTROLLING CONIFEROUS PLANTS

(75) Inventors: Joseph Zawierucha, Cary, NC (US); Glenn W. Oliver, Apex, NC (US); Harold E. Quicke, Auburn, AL (US)

(73) Assignee: BASF Aktiengesellschaft, Ludwigshafen (DE)

( * ) Notice: Subject to any disclaimer, the term of this patent is extended or adjusted under 35 U.S.C. 154(b) by 1526 days.

(21) Appl. No.: 10/583,364

(22) PCT Filed: Dec. 17, 2004

(86) PCT No.: PCT/EP2004/014424
§ 371 (c)(1), (2), (4) Date: Jun. 19, 2006

(87) PCT Pub. No.: WO2005/058041
PCT Pub. Date: Jun. 30, 2005

(65) Prior Publication Data
US 2008/0132414 A1   Jun. 5, 2008

Related U.S. Application Data

(60) Provisional application No. 60/530,657, filed on Dec. 19, 2003.

(51) Int. Cl.
*A01N 43/00* (2006.01)

(52) U.S. Cl.
USPC .......................................... 504/139; 504/130

(58) Field of Classification Search
USPC .......................................... 504/101, 130, 139
See application file for complete search history.

(56) References Cited

U.S. PATENT DOCUMENTS

| | | | |
|---|---|---|---|
| 6,054,410 A * | 4/2000 | Landes et al. | 504/134 |
| 6,444,613 B1 | 9/2002 | Feurer et al. | |
| 2001/0031704 A1 * | 10/2001 | Hacker et al. | 504/127 |
| 2003/0148887 A1 * | 8/2003 | Bratz et al. | 504/197 |

FOREIGN PATENT DOCUMENTS

| | | |
|---|---|---|
| DE | 199 51 428 A1 | 5/2001 |
| WO | WO 94/09629 A | 5/1994 |
| WO | WO 96/03878 A | 2/1996 |
| WO | WO 02/17719 A | 3/2002 |

OTHER PUBLICATIONS

Maclaren, P., Chemical thinning of radiata pine, Forest research, 1999.*
Yeiser, J.L.: "Wildling Pine Control with R6447, Oust, and Krenite S Combinations" Proceedings, Southern Weed Science Society, vol. 54, 2001, pp. 94-98.
Yeiser, J.L.: "Screening Krovar IDF, R6447 (Azafenidin) and Krenite S for Wildling Pine Control" Proceedings, Southern Weed Science Society,vol. 53, 2000, pp. 133-137.
Dayan F E et al: "Selectivity and Mode of Action of Carfentrazone-Ethyl, A Novel Phenyl Triazolinone Herbicide" Pesticide Science,Elsevier Applied Science Publisher. Barking, GB, vol. 51, No. 1, Sep. 1997, pp. 65-73.
Murai,S et al: "Synthesis and herbicidal activity of sulfonyl ureas;SL-950 and its related compounds" Journal of Pesticide Science, vol. 20, No. 4, 1995,pp. 453-462.
Ikeguchi Masahiko et al: "Synthesis and structure-activity relationships of herbicidal thiophene sulfonylurea compounds"Journal of Pesticide Science, vol. 22, No. 3, 1997, pp. 208-217.
Patent Abstracts of Japan vol. 1999, No. 12, Oct. 29, 1999 & JP 11 199412 A (Nissan Chem Ind Ltd),Jul. 27, 1999 abstract.
Pellerin Kristie J et al:"Herbicide mixtures in water-seeded imidazolinone-resistant rice (*Oryza sativa*)."Weed Technology,vol. 17, No. 4, Oct. 2003, pp. 836-841.
Dominique et al; Database CA 'Online! Chemical Abstracts Service, Columbus, Ohio, US; 2000,Lepiece,"Florasulam Primus,a new selective herbicide for the control of broad-leaved weeds in young grass".
Adamczewski, Kazimierz et al: Database CA 'Online! Chemical Abstracts Service, Columbus, Ohio, US; 1999, "The weed control efficacy of carfentrazone ethyl in winter cereals".
Sison, Chesed M.: Database CA 'Online! Chemical Abstracts Service, Columbus, Ohio, US; 2001,"Sulfentrazone for preplant weed control in pineapple".

* cited by examiner

*Primary Examiner* — Fereydoun G Sajjadi
*Assistant Examiner* — Danielle Sullivan
(74) *Attorney, Agent, or Firm* — Rothwell, Figg, Ernst & Manbeck, P.C.

(57) ABSTRACT

The present invention relates to a method for controlling coniferous plants, in particular naturally seeded coniferous plants (wildling conifers), wherein an effective amount of at least one herbicide selected from the group consisting of sulfentrazone, carfentrazone, their agriculturally acceptable salts and their agriculturally acceptable derivatives is applied to the coniferous plants to be controlled or to their parts, such as roots, leaves, seeds or germinants.

16 Claims, No Drawings

METHOD FOR CONTROLLING CONIFEROUS PLANTS

CROSS REFERENCE TO RELATED APPLICATION

This application is a 35 USC §371 National Phase Entry Application from PCT/EP2004/014424, filed Dec. 17, 2004, and designating the United States, which claims the benefit of U.S. Provisional 60/530,657, filed Dec. 19, 2003.

The present invention relates to a method for controlling coniferous plants, in particular naturally seeded conifer plants (wildling conifer) and especially for controlling wildling pine, i.e. naturally seeded pine plants.

The control of naturally seeded coniferous plants (wildling conifer control) has become an important issue in forestry. In conifer plantations and especially in pine plantations naturally seeded coniferous plants (wildlings) compete with planted ones. However, these wildlings are genetically inferior and result in sub-optimal stand density.

It is expected that the problem of wildling conifers will increase in the future for the following reasons: the use of fire to control wildling conifers in site preparation has been severely restricted by the government, the use of mechanical site preparation has diminished; the adoption of intensive management including vegetation control, fertilization and thinning is increasing the number of wild germinants and seedlings in existing stands and after harvest; with small harvesting areas becoming increasingly common, overseedings from neighbouring stands and overstocking of young plantations become more prevalent. Therefore, forest managers need a treatment that controls these unwanted wildling seedlings and releases genetically improved, newly planted conifer seedlings with no or marginal damage.

The major compounds currently used for wildling conifer control in conifer plantations include glyphosate and fosamine. Both compounds require high application rates. Moreover, lack of consistency in control is an issue with glyphosate.

F. L. Yeiser reported in "Proceedings of Southern Weed Science Society", vol. 53, pp 153 ff. about the use of commercial bromacil/diuron mixtures and of azafenidin in wildling pine control. However, the achieved control was only similar to control achieved by sulfometuron-methyl which is used in forestry for conventional weed control. Same author reported in "Proceedings of Southern Weed Science Society" vol. 54 (2001), section IV, p. 94 to 98 about investigations on wildling pine control by combined pre- and post-emergence treatments with sulfometuron, fosamine, azafenedin and azafenedin/sulfometuron-methyl mixtures. However, control of pine germination by these methods was inadequate.

Therefore, it is an objective of the present invention to provide compounds that allow a reliable and effective wildling conifer control. Moreover, these compounds should release newly planted conifer seedlings without or with only slight damaging. Surprisingly, it was found that this object could be achieved by a herbicidally active composition which comprises at least one herbicide selected from the group consisting of sulfentrazone, carfentrazone, their agriculturally acceptable salts and their agriculturally acceptable derivatives.

These compositions allow an effective control of wildling conifers, in particular of wildlings which belong to the pinaceae family and especially the control of wildling pine species (generally referred to as wildling pine control). Moreover, the compositions of the present invention lead to a reduction of undesired weeds and thus facilitate the growth of the planted coniferous plants.

Therefore, the present invention provides a method for controlling coniferous plants, in particular naturally seeded coniferous plants (wildling conifers), wherein an effective amount of at least one herbicide selected from the group consisting of sulfentrazone, carfentrazone, their agriculturally acceptable salts and their agriculturally acceptable derivatives is applied to the coniferous plants to be controlled or to their parts, such as roots, leaves, seeds or germinants.

It has been proven advantageous to apply sulfentrazone, carfentrazone, their agriculturally acceptable salts or their agriculturally acceptable derivatives (hereinafter also referred to as herbicide B) together with at least one further herbicide A which is selected from the group consisting of
A1 acetolactate synthase inhibitors (ALS inhibitors);
A2 photosynthesis inhibitors;
A3 enolpyruvyl shikimate 3-phosphate synthase inhibitors (EPSP inhibitors);
A4 glutamine synthetase inhibitors;
A5 auxin herbicides; and
A6 fosamine.

Most of these compositions are new, except for compositions which comprise at least one herbicide A selected from chlorimuron, halosulfuron, metsulfuron, nicosulfuron, primisulfuron, prosulfuron, thifensulfuron, tribenuron, imazamethabenz, flumetsulam, pyrithiobac, atrazin, difenzoquat, paraquat, bromoxynil, pyridate, glyphosate, glufosinate, 2,4-D, MCPA, dicamba, clopyralid, fluoxazine, the agriculturally acceptable salts thereof and the agriculturally acceptable derivatives thereof, and carfentrazone, an agriculturally acceptable salt thereof or an agriculturally acceptable derivative thereof, and also except for compositions which comprise at least one herbicide A selected from chlorimuron, rimsulfuron, tribenuron, imazethapyr, cloransulam, flumetsulam, metribuzin, qlyphosate, 2,4-D, the agriculturally acceptable salts thereof and the agriculturally acceptable derivatives thereof, and sulfentrazone, an agriculturally acceptable salt thereof or an agriculturally acceptable derivative thereof.

Therefore, the present invention also provides novel herbicidal compositions, which comprise at least one further herbicide A which is selected from the group consisting of
A1 acetolactate synthase inhibitors (ALS inhibitors);
A2 photosynthesis inhibitors;
A3 enolpyruvyl shikimate 3-phosphate synthase inhibitors (EPSP inhibitors);
A4 glutamine synthetase inhibitors;
A5 auxin herbicides; and
A6 fosamine.

except for compositions which comprise at least one herbicide A selected from chlorimuron, halosulfuron, metsulfuron, nicosulfuron, primisulfuron, prosulfuron, thifensulfuron, tribenuron, imazamethabenz, flumetsulam, pyrithiobac, atrazin, difenzoquat, paraquat, bromoxynil, pyridate, qlyphosate, glufonsinate, 2,4-D, MCPA, dicamba, clopyralid, fluoxazine, the agriculturally acceptable salts thereof and the agriculturally acceptable derivatives thereof, and carfentrazone, an agriculturally acceptable salt thereof or an agriculturally acceptable derivative thereof, and also except for compositions which comprise at least one herbicide A selected from chlorimuron, rimsulfuron, tribenuron, imazethapyr, cloransulam, flumetsulam, metribuzin, qlyphosate, 2,4-D, the agriculturally acceptable salts thereof and the agriculturally acceptable derivatives thereof, and sulfentrazone, an agriculturally acceptable salt thereof or an agriculturally acceptable derivative thereof.

The herbicides A of groups A1 to A6 are known from literature; see, for example The Compendium of Pesticide Common Names (http://www.hclrss.demon.co.uk/index.html); Crop Protection Handbook 2004 Vol. 90, Meister Media Worldwide, 2004; B. Hock, C. Fedtke, R. R. Schmidt, Herbizide, Georg Thieme Verlag, Stuttgart 1995; K. Vencill, Herbicide Handbook, 8$^{th}$ Edition, Weed Science Society of America, 2002.

Examples for herbicides A optionally applied according to the present invention are:

A1 from the group of the ALS inhibitors:
 amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imidazolinone herbicides such as imazamethabenz, imazamox, imazapic, imazapyr, imazaquin and imazethapyr, furthermore cloransulam, diclosulam, florasulam, flumetsulam, metosulam, penoxsulam, bispyribac, pyriminobac, propoxycarbazone, flucarbazone, pyribenzoxim, pyriftalid and pyrithiobac;

A2 from the group of the photosynthesis inhibitors:
 atraton, atrazine, ametryne, aziprotryne, cyanazine, cyanatryn, chlorazine, cyprazine, desmetryne, dimethametryne, dipropetryn, eglinazine, ipazine, mesoprazine, methometon, methoprotryne, procyazine, proglinazine, prometon, prometryne, propazine, sebuthylazine, secbumeton, simazine, simeton, simetryne, terbumeton, terbuthylazine, terbutryne, trietazine, ametridione, amibuzin, hexazinone, isomethiozin, metamitron, metribuzin, bromacil, isocil, lenacil, terbacil, brompyrazon, chloridazon, dimidazon, desmedipham, phenisopham, phenmedipham, phenmedipham-ethyl, benzthiazuron, buthiuron, ethidimuron, isouron, methabenzthiazuron, monoisouron, tebuthiuron, thiazafluron, anisuron, buturon, chlorbromuron, chloreturon, chlorotoluron, chloroxuron, difenoxuron, dimefuron, diuron, fenuron, fluometuron, fluothiuron, isoproturon, linuron, methiuron, metobenzuron, metobromuron, metoxuron, monolinuron, monuron, neburon, parafluron, phenobenzuron, siduron, tetrafluron, thidiazuron, cyperquat, diethamquat, difenzoquat, diquat, morfamquat, paraquat, bromobonil, bromoxynil, chloroxynil, iodobonil, ioxynil, amicarbazone, bromofenoxim, flumezin, methazole, bentazon, propanil, pentanochlor, pyridate, and pyridafol;

A3 from the group of the EPSP synthase inhibitors: glyphosate;

A4 from the group of the glutamine synthase inhibitors: glufosinate and bilanaphos;

A5 from the group of the auxin herbicides:
 clomeprop, 2,4-D, 2,4,5-T, MCPA, MCPA thioethyl, dichlorprop, dichlorprop-P, mecoprop, mecoprop-P, 2,4-DB, MCPB, chloramben, dicamba, 2,3,6-TBA, tricamba, quinclorac, quinmerac, aminopyralid, clopyralid, fluroxypyr, picloram, triclopyr and benazolin;

A6 fosamine.

Amongst herbicides A of groups A1 to A6 the compounds listed below and their agriculturally acceptable salts and, in the case of compounds having a carboxyl group, also their agriculturally acceptable derivatives are especially preferred:

A1 amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imidazolinoe herbicides such as imazamethabenz, imazamox, imazapic, imazapyr, imazaquin and imazethapyr, furthermore cloransulam, diclosulam, florasulam, flumetsulam, metosulam, penoxsulam, bispyribac, pyriminobac, propoxycarbazone, pyribenzoxim, pyriftalid and pyrithiobac;

A2 atrazine, ametryne, cyanazine, simazine, hexazinone, metribuzin, tebuthiuron, diuron, bromoxynil and paraquat;

A3 glyphosate;

A4 glufosinate;

A5 2,4-D, 2,4-DB, dichlorprop, dichlorprop-P, MCPA, MCPB, mecoprop, mecoprop-P, dicamba, quinclorac, quinmerac, aminopyralid, clopyralid, fluroxypyr, picloram, triclopyr, benazolin; and A6 fosamine.

Among the compositions applied according to the invention, particular preference is given to those compositions which comprise at least one herbicide A selected from groups A1, A3, A4, A5 and A6, in particular at least one herbicide A selected from groups A1, A3 and A4, and at least one further herbicide B selected from the group consisting of sulfentrazone, carfentrazone, the agriculturally acceptable salts thereof and the agriculturally acceptable derivatives thereof, and sulfentrazone, an agriculturally acceptable salt thereof or an agriculturally acceptable derivative thereof.

A first particularly preferred embodiment of the invention relates to a method, wherein a) at least one herbicide A, which is selected from imidazolinone herbicides, and b) at least one further herbicide B, which is selected from the group consisting of sulfentrazone, carfentrazone, their agriculturally acceptable salts and their agriculturally acceptable derivatives is applied to the coniferous plants to be controlled or to their parts, such as roots, leaves, seeds or germinants.

Suitable imidazolinone herbicides comprise imazethabenz, imazamox, imazapic, imazapyr, imazaquin and imazethapyr, with preference given to imazamox, imazapic and imazapyr, and particular preference being given to imazapyr.

In another particularly preferred embodiment of the invention, preference is given to the application of those compositions which comprise at least one, preferably especially exactly one herbicidally active compound of the group A1, in particular selected from the group consisting of metsulfuron and sulfometuron, in combination with at least one, preferably especially exactly one further herbicide B.

In another particularly preferred embodiment of the invention, preference is given to the application of those compositions which comprise at least one, preferably especially exactly one herbicidally active compound of the group A2, in particular selected from the group consisting of atrazine, cyanazine, hexazione, diuron, bromoxynil and paraquat, in combination with at least one, preferably especially exactly one further herbicide B.

In another particularly preferred embodiment of the invention, preference is given to the application of those compositions which comprise at least one, preferably especially exactly one herbicidally active compound of the group A3, in particular glyphosate, in combination with at least one, preferably especially exactly one further herbicide B.

In another particularly preferred embodiment of the invention, preference is given to the application of those compositions which comprise at least one, preferably especially exactly one herbicidally active compound of the group A4, in particular glufosinate, in combination with at least one, preferably especially exactly one further herbicide B.

In another particularly preferred embodiment of the invention, preference is given to the application of those compositions which comprise at least one, preferably especially exactly one herbicidally active compound of the group A5, in particular selected from the group consisting of 2,4-D, dicamba, aminopyralid, clopyralid, fluoroxypyr, picloram and triclopyr, in combination with at least one, preferably especially exactly one further herbicide B.

In another particularly preferred embodiment of the invention, preference is given to the application of those compositions which comprise fosamine in combination with at least one, preferably especially exactly one further herbicide B.

Among the compositions applied according to the invention, particular preference is especially given to the application of those compositions which comprise at least one, preferably especially exactly one herbicidally active compound selected from the group consisting of metsulfuron, sulfometuron, imazapyr, hexazione, paraquat, glyphosate, glufosinate, 2,4-D, dicamba, aminopyralid, clopyralid, picloram, triclopyr and fosamine, in combination with at least one, preferably especially exactly one further herbicide B.

Particular preference is given, for example, to the application of those compositions which comprise a herbicide A listed in one row of table 1 and sulfentrazone, an agriculturally acceptable salt or derivative thereof (compositions 1.1 to 1.14).

TABLE 1

| Composition No. | Herbicide A |
|---|---|
| 1.1 | metsulfuron |
| 1.2 | sulfometuron |
| 1.3 | imazapyr |
| 1.4 | hexazione |
| 1.5 | paraquat |
| 1.6 | glyphosate |
| 1.7 | glufosinate |
| 1.8 | 2,4-D |
| 1.9 | dicamba |
| 1.10 | aminopyralid |
| 1.11 | clopyralid |
| 1.12 | picloram |
| 1.13 | triclopyr |
| 1.14 | fosamine |

Preference is also given to the application of compositions 2.1-2.14 which differ from the corresponding compositions 1.1-1.14 only in that sulfentrazone is replaced by carfentrazone an agriculturally acceptable salt or derivative thereof. Preferred herbicide B is carfentrazone an agriculturally acceptable salt or an agriculturally acceptable derivative thereof.

Since some of the aforementioned herbicides A, in particular the imadizolinone herbicides, and carfentrazone have an acidic carboxyl group, they may also be applied as their agriculturally acceptable salts or as their agriculturally acceptable derivatives.

The agriculturally acceptable salts of the herbicides A as well as of carfentrazone comprise at least one agriculturally acceptable counter ion. Suitable counterions are alkalimetal ions, e.g. lithium, sodium or potassium ions, alkaline earth metal ions, e.g. calcium or magnesium ions, ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, $C_3$-$C_6$-cycloalkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, dicyclohexylammonium, tris(2-hydroxyethyl)ammonium, 2-hydroxyethylammonium, 2-(2-hydroxyethoxy)ethylammonium, bis(2-hydroxyethyl)ammonium, benzyltrimethylammonium and benzyltriethylammonium.

It is also possible to use the herbicides A as their agriculturally acceptable derivatives, e.g. as amides such as primary amides, mono- or di-$C_1$-$C_6$-alkylamides, anilides or preferably as esters, e.g. as allylesters, propagylesters, $C_1$-$C_8$-alkylesters, $C_1$-$C_4$-alkoxy-$C_1$-$C_4$-alkylesters and also as thioesters. Preferred derivates of herbicides A and of carfentrazone, respectively, are the aforementioned esters, in particular the alkyl esters and the alkoxyalkyl esters and especially the methyl, ethyl, isopropyl, isobuyl, 2-butoxyethyl, 2-butoxy-1-methylethyl, 1-methylheptyl, isooctyl, 1-methylhexyl or 2-ethoxyethyl esters such as carfentrazone ethyl.

In the method of the invention herbicide B and optionally herbicide A can be applied jointly or separately, i.e. simultaneously or successively. In order to achieve more effective control of the naturally seeded coniferous plants, it is only required that the herbicide A and the herbicide B affect the coniferous plants to be controlled or their parts at the same time. The term "coniferous plants to be controlled or their parts" is understood to comprise naturally seeded conifer seedlings, their roots, cones and leaves as well as their seeds and their germinants. Consequently, the herbicidal composition of the invention can be formulated in one formulation that comprises both herbicides A and B as well as in two separate formulations as a two-kits-of-parts, i.e. one formulation comprises herbicide A and the other comprises herbicide B. These two separate formulations can be mixed before applying them and thus herbicides A and B are applied jointly. However these two formulations may also be applied seperately, provided that herbicide A and herbicide B act at the same time on the plants to be controlled or on their parts. It is, however, preferable to apply herbicides A and B jointly.

The amount of herbicide B which is necessary to achieve an effective control will in general vary from 10 g/ha to 500 g/ha, preferably from 50 g/ha to 450 g/ha and ideally from 200 g/ha to 450 g/ha. Here and in the following the amounts given for herbicides A and B refer to the active portion of the herbicide molecule. Thus in the case of salts or derivatives the amounts refer to the free acid.

In the preferred method of the present invention the herbicide A is usually applied in amounts from 100 g/ha to 1400 g/ha, more preferably from 400 g/ha to 1400 g/ha and ideally from 500 g/ha to 900 g/ha.

Preferably, the herbicide A and the herbicide B will be applied in a weight ratio A:B ranging from 200:1 to 1:5, more preferably from 100:1 to 1:2 and ideally from 30:1 to 1:1. The compositions of the invention preferably contain herbicide A and herbicide B in weight ratio A:B ranging from 200:1 to 1:5, preferably from 100:1 to 1:2 and ideally from 30:1 to 1:1.

Herbicides A and B may be applied by any means which are customary in the field of crop-protection and especially in the field of forestry. Herbicides A and B may be applied, for example, in the form of directly sprayable aqueous emulsions, suspensions as directly sprayable powders and dusts, and also as highly-concentrated aqueous, oily or other suspensions or dispersions, as oil dispersions or as granules. Depending on the kind of formulation they will be applied by means of spraying, atomizing, dusting, broadcasting or watering. The person skilled in the art is sufficiently familiar with useful formulations and means of applying them. In any case, those formulation and the means of applying them should ensure the finest possible distribution of the active compounds A and B.

In order to achieve wildling conifer control, herbicides B and optionally A are preferably applied to the naturally seeded coniferous seedlings as a whole or to their roots or leaves. However herbicides B and optionally A can be also applied to the germinants of the conifers to be controlled. In a preferred embodiment of the invention, control is achieved by applying herbicides B and optionally A after germination of the wildling seed, i.e. by post-emergence treatment of the wild conifer seedlings.

Herbicides B and optionally A are applied to the area to be protected from wildling conifer mainly by spraying. Application can be carried out by customary spraying techniques using, for example, water as carrier and spray liquor rates ranging from about 50 to 1 000 l/ha (for example from 100 to 300 l/ha). Application of herbicides B and optionally A by the low-volume and the ultra-low-volume method is possible, as is their application in the form of microgranules.

Application of herbicides B and optionally A can be done by over-the-top treatment of the wildlings or by directed treatment of the wildlings, e.g. by directed or spot-spraying.

Preferably, the herbicides B and optionally A are applied during site-preparation, i.e. before the conifer seedlings are planted. However it is also possible to apply herbicides B and optionally A in conifer plantations, i.e. in the presence of planted conifer seedlings or trees. In this case, herbicides B and optionally A are preferably applied by directed treatment of the wildings in order to leave the planted seedlings or trees unaffected.

Preferably herbicides B and optionally A are applied in the site-preparation of pine plantations, and especially the site-preparation for plantations of pine species selected from *P. banksiana, P. clausa, P. contorta, P. echinata, P. elliottii, P. lambertina, P. palustris, P. glabra, P. ponderosa, P. pungens, P. rigida, P. resinosa, P. serotina, P. strobus, P. taeda, P. virginiana*.

In particular, the method of the invention comprises at least one application of herbicides B and optionally A within 1 year and ideally within 10 month prior to planting of the conifer seedlings. More preferably herbicides B and optionally A are applied within the period from 3 to 10 month and especially from 6 to 10 month prior to planting of the conifer seedlings. However, it is also possible to apply herbicides B and optionally A shortly before or up to the day when the conifer seedlings are planted. Preferably herbicides B and optionally A are applied in spring or in summer, more preferably from the beginning of March until the end of August in the northern hemisphere or from beginning of September until the end of February in the southern hemisphere. The application of herbicides B and optionally A can be repeated once, twice or more often until the conifer seedlings are planted. The periods between each application may vary from 0,5 month to 6 month. However, generally one application is sufficient. In case of several applications it is preferable that the total application rate of all applications does not exceed the above given maximum application rates.

Depending on the form in which the ready-to-use preparations are present in the compositions according to the invention, they comprise one or more liquid or solid carriers, if appropriate, surfactants and, if appropriate, further auxiliaries which are customary for formulating crop protection products. The person skilled in the art is sufficiently familiar with the recipes for such formulations.

Suitable inert auxiliaries with carrier function are e.g.:
liquid carriers such as mineral oil fractions with a medium to high boiling point, such as kerosine and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water, and
solid carriers such as mineral earths e.g. silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders, or other solid carriers.

Suitable auxiliaries comprise any auxiliaries which are usually employed in formulations of herbicides, e.g. tackifiers, anti-oxidants, preservatives, rheology modifiers such as thickeners, anti-freezes, defoamers and surface active substances.

The latter comprise emulsifiers, protective colloids, wetting agents, anti-settling agents and dispersants that are normally employed in agricultural formulations of herbicides. The surface-active substances may be nonionic, anionic and/or cationic. Suitable surfactants which may be used in the compositions of the invention are disclosed e.g. in "McCutcheon's Detergents and Emulsifiers Annual", MC Publishing Corp., Ridgewood, N.J., USA 1981; H. Stache, "Tensid-Taschenbuch", $2^{nd}$ ed., C. Hanser, Munich, Vienna, 1981; M. and J. Ash, "Encyclopedia of Surfactants", vol. I-III, Chemical Publishing Co., New York, N.Y., USA 1980-1981. Suitable surfactants are e.g. the alkali metal salts, alkaline earth metal salts and ammonium salts of aromatic sulfonic acids, e.g. ligno-, phenol-, naphthalene- and dibutylnaphthalenesulfonic acid, and of fatty acids, of alkyl- and alkylarylsulfonates, of alkyl sulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ether or polyoxypropylene alkyl ether, lauryl alcohol polyglycol ether acetate, sorbitol esters, lignosulfite waste liquors or methylcellulose.

Suitable thickening agents include inorganic thickening agents, such as clays, hydrated magnesium silicates and organic thickening agents, such as polysaccharide gums, like xanthan gum, guar gum, gum arabic and cellulose derivatives. Suitable preservatives to prevent microbial spoiling of the compositions of the invention include formaldehyde, alkyl esters of p-hydroxybenzoic acid, sodium benzoate, 2-bromo- 2-nitropropane-1,3-diol, o-phenylphenol, thiazolinones, such as benzisothiazolinone, 5-chloro-2-methyl-4-isothiazolinone, pentachlorophenol, 2,4-dichlorobenzyl alcohol and mixtures thereof. Suitable anti-freezing agents include organic solvents which are completely miscible with water, such as ethylene glycol, propylene glycol, other glycols, glycerin or urea. Suitable defoamers include polysiloxanes, such as polydimethyl siloxane.

Aqueous use forms of herbicides A and B can be prepared from emulsion concentrates, suspensions, pastes, wettable powders or water-dispersible granules by adding water. To prepare emulsions, pastes or oil dispersions, herbicides A and B as such or dissolved in an oil or solvent, can be homogenized in water by means of a wetting agent, tackifier, dispersant or emulsifier. Alternatively, it is also possible to prepare concentrates comprising the active substance, wetting agent, tackifier, dispersant or emulsifier and, if desired, solvent or oil, and these concentrates are suitable for dilution with water.

Powders, materials for spreading and dusts can be prepared by mixing or concomitantly grinding the active substances with a solid carrier.

Granules, e.g. coated granules, impregnated granules and homogeneous granules, can be prepared by binding the active compounds to solid carriers. The concentrations of the active compounds in the ready-to-use preparations can be varied within wide ranges. In general, the compositions of the invention comprise approximately from 0.001 to 98% by weight, preferably 0.01 to 95% by weight, of active compounds. The active compounds are employed in a purity ranging from 90% to 100%, preferably 95% to 100% (according to NMR spectrum).

The compositions according to the invention can, for example, be formulated as follows:

I 20 parts by weight of the active compound or active compound mixture in question are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active compound.

II 20 parts by weight of the active compound or active compound mixture in question are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active compound.

III 20 parts by weight of the active compound or active compound mixture in question are dissolved in a mixture composed of 25 parts by weight of cyclohexanone, 65 parts by weight of a mineral oil fraction with a boiling point of 210 to 280° C. and 10 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active compound.

IV 20 parts by weight of the active compound or active compound mixture in question are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20 000 parts by weight of water gives a spray mixture which comprises 0.1% by weight of the active compound.

V 3 parts by weight of the active compound or active compound mixture in question are mixed with 97 parts by weight of finely divided kaolin. This gives a dust which comprises 3% by weight of the active compound.

VI 20 parts by weight of the active compound or active compound mixture in question are mixed intimately with 2 parts by weight of calcium dodecylbenzenesulfonate, 8 parts by weight of fatty alcohol polyglycol ether, 2 parts by weight of the sodium salt of a phenol-urea-formaldehyde condensate and 68 parts by weight of a paraffinic mineral oil. This gives a stable oily dispersion.

VII 1 part by weight of the active compound or active compound mixture in question is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII 1 part by weight of the active compound or active compound mixture in question is dissolved in a mixture composed of 80 parts by weight of cyclohexanone and 20 parts by weight of Wettol® EM 31 (nonionic emulsifier based on ethoxylated castor oil). This gives a stable emulsion concentrate.

The compositions as well as the method according to the present invention are suitable for controlling naturally seeded coniferous plants, in particular wildling plants belonging to the family of pinaceae. They are especially useful for controlling wildling conifer plants belonging to the genus of *pinus*, in particular those of the subgenera *P. contortae, P. australes, P. sylvestres* and *P. strobi*, e.g. wildlings of the species *P. banksiana, P. clausa, P. contorta, P. echinata, P. elliottii, P. lambertina, P. ponderosa, P. glabra, P. palustris, P. pungens, P. rigida, P. resinosa, P. serotina, P. strobus, P. taeda* or *P. virginiana*. The method of the invention is particularly useful for controlling the pine species *P. banksiana, P. echinata, P. elliottii, P. lambertina, P. palustris, P. rigada, P. ponderosa, P. contorta, P. strobus, P. taeda* and *P. virginia*.

The compositions as well as the method according to the present invention are also useful for controlling other undesirable vegetation in forestry, in particular herbaceous weeds such as *Amaranthus* spp., *Ipomoea lacunosa, Ipomoea hederacea, Ambrosia artemisiifolia, Solanum ptycanthum, Campsis radicans* etc. Thereby, planting of conifer seedlings as well as its growth are faciliated.

Moreover, it may be useful to apply the compositions according to the invention jointly as a mixture with other crop protection products, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates may also be added.

The invention is further illustrated by the following examples.

The effect of the herbicidal mixtures according to the invention on the growth of wildling conifer, in particular wildling pine (*Pinus* spp.) was demonstrated by the following greenhouse and field experiments:

Greenhouse Experiments:

For the following experiments herbicides A and B were applied as an aqueous spray liquor, which was prepared from their commercially available formulations. Herbicide A (imazapyr as its isopropylammonium salt) was used as an emulsifiable concentrate (240 grams acid eq/l; CHOPPER® from BASF Corporation). Component B (carfentrazone) was used as a wettable granule (40% by weight; AIM®, from FMC). Methylated seed oil (MSO) was also added to the spray liquor in amounts of 5% volume/volume as a standard spray adjuvant. Water was used as the carrier.

The spray liquor had the following general recipe:

| | | |
|---|---|---|
| Herbicide A (imazapyr) | 12.5 ml/L | 0.56 kg active/ha |
| Herbicide B (carfentrazone) | 6.0 g/L | 0.45 kg active/ha |
| methylated seed oil | 50.0 ml/L | 5.0% v/v |

Wildling pine of the variety Loblolly (*Pinus taeda* L.) were first grown to a height of 50 to 60 cm (one yr old seedlings) and then postemergence herbicide applications were made. Here, the herbicidal compositions were suspended or emulsified in water as distribution medium to obtain a spray liquor, which was sprayed on the wildlings by using finely distributing nozzles, e.g. even flat fan spray nozzles. Spray liquor rate was 183 l/ha. The experiment was set up as a completely random design with four replications (one seedling per replication).

The test period extended over 30 days at 27° C. During this time, the plants were tended, and their response to the treatments with the active compound was evaluated.

The evaluation for the damage caused by the chemical compositions was carried out using a scale from 0 to 100%, compared to the untreated control plants. Here, 0 means no damage and 100 means complete destruction of the plants. The results are presented in table 1.

TABLE 1

| Treatment | Rate kg active/ha* | Loblolly Pine % control** |
|---|---|---|
| Control | — | 0 |
| Imazapyr | 0.56 | 0 |
| Imazapyr + Carfentrazone | 0.56 + 0.45 | 84 |

*means of four replications

The data in Table 1 show that carfentrazone+imazapyr provided increased control of the loblolly pine seedlings at day 30 after treatment.

Field Experiments

For the following experiments herbicides A and B were applied as an aqueous spray liquor, which was prepared from their commercially available formulations. Herbicide A (imazapyr as its isopropylammonium salt) was used as an emulsifiable concentrate (240 grams acid eq/l; CHOPPER® from BASF Corporation). Component B (carfentrazone) was used as a wettable granule (40% by weight; AIM®, from FMC). Methylated seed oil (MSO) was also added to the spray liquor in amounts of 12,5% volume/volume as a standard spray adjuvant. Water was used as the carrier.

The spray liquor had the following general recipe:

| | | |
|---|---|---|
| Herbicide A (imazapyr) | 12.5 ml/L | 0.56 kg active/ha |
| Herbicide B (carfentrazone) | 0.75-6.0 g/L | 0.056-0.45 kg active/ha |
| methylated seed oil | 125.0 ml/L | 12.5% v/v |

Site One

The test site selected consisted of a population of wildling pine of the variety Slash (*Pinus elliottii*) that were allowed to grow to a height of 90 to 150 cm (2 yr old seedlings) and then treated. Here, the herbicidal compositions were suspended or emulsified in water as the distribution medium and sprayed using finely distributing nozzles, e.g. flat fan spray nozzles. Spray liquor rate was 183 l/ha. Experiment design used was a randomized complete block design with three replications (5 seedling per replication).

The test period extended over 163 days. During this time, response to the treatments with the active compound was evaluated.

The evaluation for the damage caused by the chemical compositions was carried out using a scale from 0 to 100%, compared to the untreated control plants. Here, 0 means no damage and 100 means complete destruction of the plants. The results are presented in table 2.

TABLE 2

| Treatment | Rate kg active/ha | Slash Pine % control* |
|---|---|---|
| Control | — | 0 |
| Imazapyr + Carfentrazone | 0.56 + 0.056 | 50 |
| Imazapyr + Carfentrazone | 0.56 + 0.220 | 93 |
| Imazapyr + Carfentrazone | 0.56 + 0.450 | 90 |

*means of three replications, ratings at 163 days after treatment

Results presented in Table 2 confirmed greenhouse results of the susceptibility of wilding pine to applications of imazapyr+carfentrazone.

Site Two

The test site selected consisted of a natural population of wildling pine of the variety Loblolly (*Pinus taeda*). Pines were 60 to 150 cm in height at treatment. Application set up was similar to that described for site one. The results are presented in table 3.

TABLE 3

| Treatment | Rate kg active/ha | Loblolly Pine % control* |
|---|---|---|
| Control | — | 0 |
| Imazapyr | 0.56 | 10 |
| Imazapyr + Carfentrazone | 0.56 + 0.220 | 80 |
| Imazapyr + Glyphosate | 0.56 + 4.5 | 60 |

*means of three replications, ratings at 82 days after treatment

Results presented in Table 3. also confirmed the susceptibility of wilding pine to applications of carfentrazone. At the 82-day rating, control with carfentrazone was superior to that of a standard glyphosate mixture.

We claim:

1. A method for controlling coniferous plants comprising applying
   a) an effective amount of at least one herbicide A, which is an imidazolinone herbicide; and
   b) an effective amount of at least one herbicide B selected from the group consisting of sulfentrazone, carfentrazone and its agriculturally acceptable salts, esters, thioesters and amides to coniferous plants to be controlled and/or to the parts of these plants, wherein the herbicide A and the herbicide B are applied in a weight ratio A:B ranging from 1:5 to 200:1.

2. The method as claimed in claim 1, wherein herbicide A is selected from imazapyr, its agriculturally acceptable salts, esters, thioesters and amides.

3. The method as claimed in claim 1, wherein herbicide B is selected from carfentrazone, its agriculturally acceptable salts, esters, thioesters and amides.

4. The method as claimed in claim 1, wherein the effective amount of herbicide B is applied during site preparation for a plantation of coniferous trees.

5. The method as claimed in claim 1, wherein the herbicide A is applied in amounts from 100 to 1400 g/ha.

6. The method as claimed in claim 1, wherein the herbicide B is applied in amounts from 10 to 500 g/ha.

7. The method as claimed in claim 1, wherein the effective amount of herbicide B is applied after emergence of the coniferous plants to be controlled.

8. The method as claimed in claim 1, wherein the coniferous plants to be controlled belong to the pinaceae family.

9. The method as claimed in claim 8, wherein the coniferous plants to be controlled are selected from the pine species consisting of *P. banksiana, P. clausa, P. echinata, P. elliotti, P. contorta, P. palustris, P. glabra, P. lambertina, P. ponderosa, P. pungens, P. rigida, P. resinosa, P. serotina, P. strobus, P. taeda* and *P. virginiana*.

10. The method as claimed in claim 1, wherein the effective amounts of herbicide B and herbicide A are applied during site preparation for a plantation of coniferous trees.

11. The method as claimed in claim 1, wherein the effective amounts of herbicide B and herbicide A are applied after emergence of the coniferous plants to be controlled.

12. The method as claimed in claim 1, wherein at least one herbicide selected from the group consisting of glyphosate, agriculturally acceptable salts, esters, thioester, and amides thereof;

is also applied in an effective amount to the coniferous plants to be controlled or to their parts.

13. The method of claim 12, wherein the effective amounts of herbicide B and herbicide A are applied during site preparation for a plantation of coniferous trees.

14. The method of claim 12, wherein the effective amounts of herbicide B and herbicide A are applied after emergence of the coniferous plants to be controlled.

15. The method of claim 1, wherein said coniferous plants are wildling pines.

16. The method of claim 1, wherein said herbicide B is sulfentrazone, its agriculturally acceptable salts, esters, thioesters or amides.

* * * * *